(12) United States Patent
Schnetzler et al.

(10) Patent No.: US 6,693,401 B1
(45) Date of Patent: Feb. 17, 2004

(54) PRECISION POSITIONING TILT DEVICE

(75) Inventors: Rene H. Schnetzler, Huntington, NY (US); Eddy Gabis, Stony Brook, NY (US)

(73) Assignee: Nutec Compnents, Inc., Deer Park, NY (US)

( * ) Notice: Subject to any disclaimer, the term of this patent is extended or adjusted under 35 U.S.C. 154(b) by 0 days.

(21) Appl. No.: 10/223,558

(22) Filed: Aug. 19, 2002

(51) Int. Cl.[7] ................................................. G05B 11/32
(52) U.S. Cl. ........................................ 318/625; 318/649
(58) Field of Search ................................. 318/625, 649, 318/652; 220/645

(56) References Cited

U.S. PATENT DOCUMENTS 6,193,099 B1 * 2/2001 Garton et al. ............... 220/645

OTHER PUBLICATIONS (M–041, M–044) TIP/TILT Stages, Catalog, "Physik Instrumente" [http://www.pi.ws].

* cited by examiner

Primary Examiner—Karen Masih
(74) Attorney, Agent, or Firm—Dilworth & Barrese, LLP

(57) ABSTRACT

A precision positioning tilt device includes an inner tilt frame directly actuated by a first motor so as to enable the tilt frame to pivot about a frame axis and a platform removably mounted on the inner tilt frame and directly actuated by a second motor so as to pivot about a platform axis extending perpendicular to and coaxial with the frame axis.

18 Claims, 3 Drawing Sheets

PRECISION POSITIONING TILT DEVICE

BACKGROUND OF THE INVENTION

1. Field of the Invention

This invention relates to a precision positioning device. In particular, the invention relates to a multi-stage module capable of displacing an element to be aligned in different planes extending along perpendicular but coplanar axes, so that the planes can be articulated relative to one another at any desired position within a desired range.

2. Description of the Related Art

Alignment stages are known and one may find their application in numerous and diverse fields. Typically, alignment stages are utilized for the positioning of elements, and are required to precisely position an element to be aligned in a desired position and to repeat the desired position at a high rate.

As a rule, an alignment stage includes numerous mechanical linkages translating different motions necessary to displace the element to be aligned in different planes. The alignment stage can be a single tilt stage, in which the element to be aligned is angularly displaceable about a single axis, or a dual alignment stage providing displacement of the element about two axes extending transversely to one another.

Typically, two actuators mounted on a dual alignment device displace a single frame along transverse axes. Known structures of such dual alignment devices have the actuators mounted in different planes, thus rendering the overall structure of the dual stage rather complicated and cumbersome.

There are, however, known multi stage alignment devices utilizing multiple actuators, which have respective axes extending in a common plane. One of such multi stage alignment devices is manufactured by "Physik Instrumente" (referred further as a PI device). The PI device has a single frame selectively tiltable about perpendicular and coplanar axes in response to actuation of two piezoelectric actuators (PZT).

While PZT drives are accurate, their structure may cause certain difficulties for the overall construction of the multi-stage alignment device. One of the known disadvantages of the PZT actuator includes a complex actuating assembly having at least one motion-translating component which converts axial displacement of the PZT actuator into angular displacement of a tilt frame supporting an element to be aligned. Thus, since the PZT drive moves along a drive axis extending perpendicular to a pivot axis of the tilt frame, precision with which the tilt frame pivots can be compromised.

Furthermore, the PZT drives utilized in the PI device are typically energized by very low voltage signals. To generate such low voltage signals, a power source has to meet certain requirements, which contribute to the relatively high cost of the PI device. Also, the PZT drives are open loop devices designed to displace a tilt frame at a very small angle, which is difficult to detect in the open loop design. As a consequence, positioning sensors mounted to verify the frame displacement can add to structural complexity and cost of the PI device.

It is, therefore, desirable to provide a precision positioning tilt device having a simple and reliable structure. Also, a precision positioning tilt device provided with a compact structure actuated by two independent closed loop servo control actuators is desirable as well. Furthermore, a precision positioning tilt device characterized by a direct mechanical link between each tilt stage, a respective servo torque motor and a respective positioning sensor is also desirable.

SUMMARY OF THE INVENTION

The above and other objects are attained by a precision positioning tilt device having a small size, which allows a high accuracy of positioning an element to be manipulated by displacing the element in two planes, which extend along mutually perpendicular, but coplanar axes. The inventive precision positioning tilt device is a limited pivotal rotary device for small 0–5° angular motion, whose use is determined by a particular practical application of the device and can include, but is not limited to, aligning surgical instruments, connecting optical components, and other operations requiring high precision positioning of elements.

The inventive precision positioning device includes an inner tilt frame operable for pivoting about a frame axis and actuating both the element to be manipulated and a platform mounted on the tilt frame to pivot with the tilt frame about the frame axis. Furthermore, the platform is operable for pivoting independently from the tilt frame about a platform axis extending transversely to the frame axis. To facilitate kinematics of the inventive precision positioning device, the frame and platform axes are coplanar providing all pivotal components of the inventive positioning device with a common geometrical center of symmetry positioned at the intersection of the axes.

In accordance with one aspect of the invention, first and second electric DC brushless servo torque motors directly actuate the tilt frame and the platform, respectively, without assistance of transitional mechanical linkages. Each of the first and second motors can be energized independently from the other motor so that the precision positioning device, in accordance with the invention, can be utilized as a single or dual tilt stage module. The use of closed loop servomotors affords high resolution and the ability to achieve single count moves with positive feedback. Another advantage of the closed loop servo system is the accommodation of various load conditions and operating modes, such as various speeds. Furthermore, the closed loop servo system is characterized by the high torque levels of the DC motors allowing fast positioning of the element to be manipulated in a desired position which is steadily registered and, if necessary, can be repeated at a high rate.

In accordance with another aspect of the invention, position feedback is provided by installing grating scales directly on the movable tilt frame and platform and having non-contacting solid-state sensors juxtaposed with the grating scales. The grating scales are fixed to and, thus, pivot synchronously with the platform and the inner tilt frame, respectively, so the measurement provided by the solid-state sensors corresponds to true displacement of the movable frame and platform.

According to still another aspect of the invention, the precision positioning tilt device has a compact and rugged design including a cavity provided in the platform and dimensioned to receive the second DC brushless motor so that a shaft is centrally positioned within the platform and fixedly mounted on the inner tilt frame. Thus, the inner tilt frame serves both as an actuator for the platform as a result of a rigid linkage between the inner tilt frame and platform, and as a support for the second motor.

BRIEF DESCRIPTION OF THE DRAWINGS

The above and other objects, advantages and features of the present invention will become more readily apparent from the detailed description of the preferred embodiments discussed in conjunction with the following drawings, in which.

DESCRIPTION OF THE PREFERRED EMBODIMENT

Figure 1:
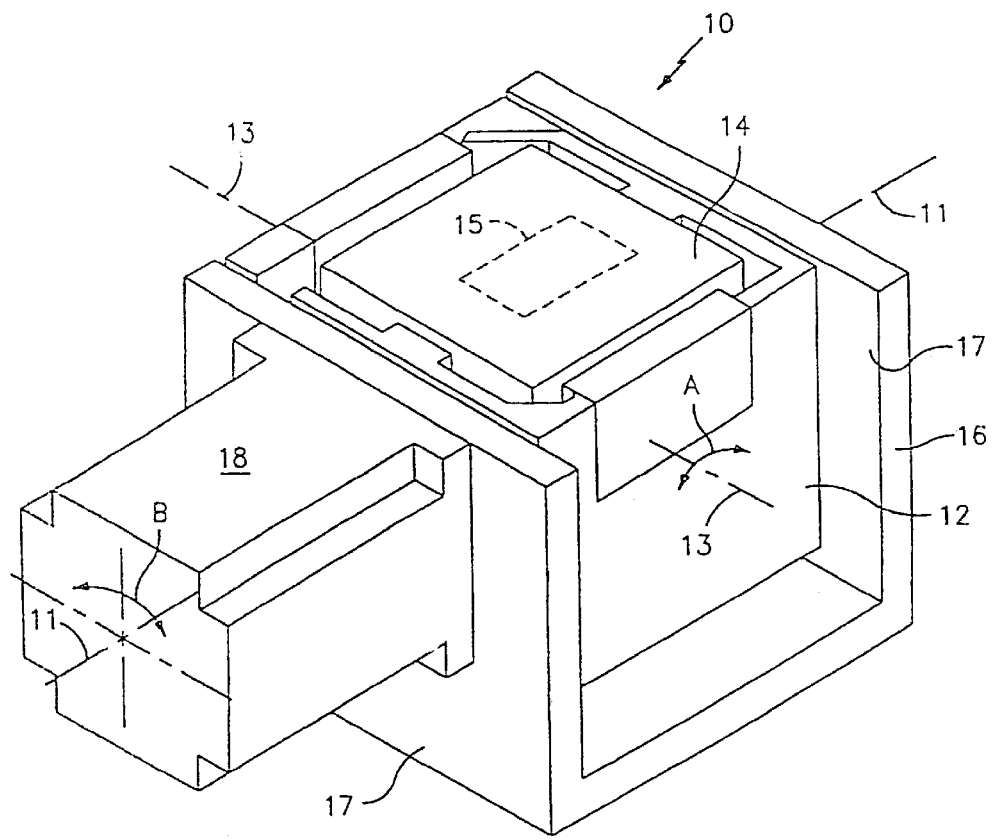
FIG. 1 is a perspective view of a precision positioning tilt device according to the invention.

Referring to FIGS. 1–5, a positioning tilt device 10 is shaped and dimensioned to facilitate alignment processes requiring high precision by providing an element 15 to be manipulated with independent tilt motion about a frame axis 11 and a platform axis 13. The frame 11 and platform 13 axes extend in the same plane and transversely to one another, so that the element 15 can be selectively angularly displaced by rotating the frame axis 11 and/or by rotating the platform axis 13.

A spatial position in which planes extending along the axes 11 and 13 coincide with one another corresponds to an initial position of the positioning tilt device 10, which, thus, has a center of symmetry lying on the intersection of the frame 11 and platform 13 axes.

Figure 2:
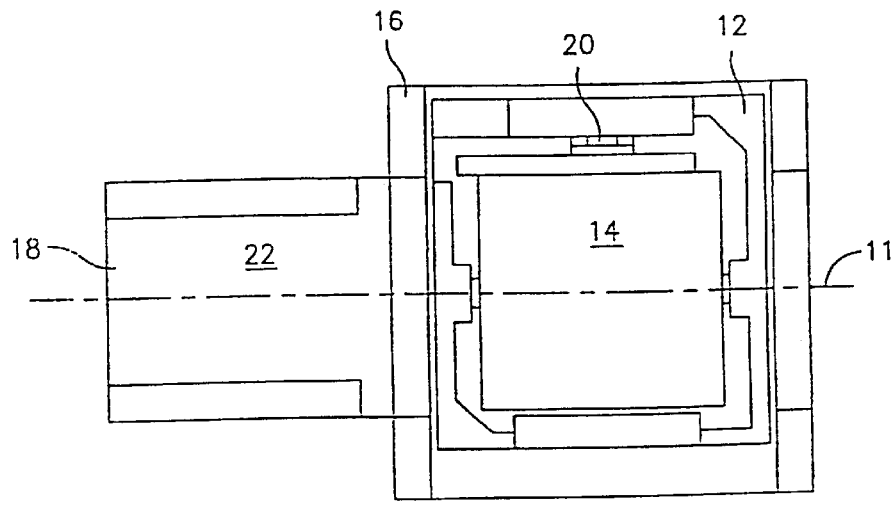
FIG. 2 is a top view of the precision positioning tilt device illustrated in FIG. 1.

The positioning tilt device 10 has an outer, stationary frame 16 which is, as illustrated in FIGS. 1 and 2, preferably polygonal and includes a plurality of side walls 17 that can be formed as a one piece element or adjoined to one another by a plurality of fasteners (not shown here). To provide displacement of the element 15 about the frame 11 and platform 13 axes, a structure including an inner tilt frame 12 and a platform 14 is mounted on the outer stationary frame 16.

The inner tilt frame 12 supports the platform 14, which carries the element 15, so that both the inner tilt frame 12 and the platform 14 pivot synchronously about the frame axis 11 and, thus, displace the element 15 in a direction B (FIG. 1). The platform 14, in turn, is capable of individually tilting about the platform axis 13 to displace the element 15 along a direction A (FIG. 1).

Figure 3:
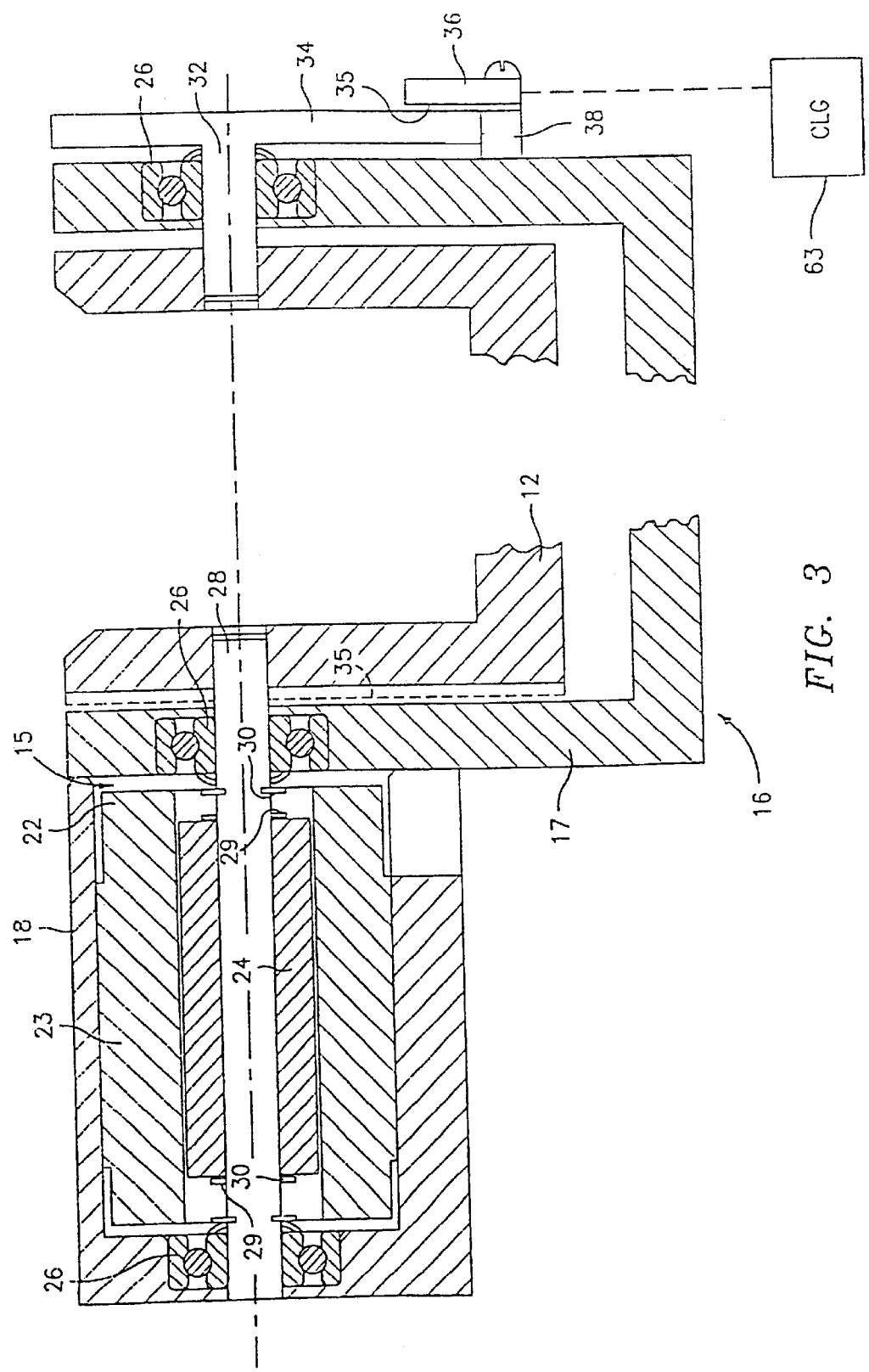
FIG. 3 is a section elevation view of the precision positioning tilt device of FIG. 1 taken along a frame axis.

Referring to FIGS. 2 and 3, actuation of the inner tilt frame 12 is accomplished by an electric DC brushless frameless servo motor 22 referred further as the first motor and mounted within a motor housing 18, which is attached to the outer frame 16 and extends outwardly therefrom along the frame axis 11. The use of the servomotor eliminates all mechanical transmission devices and provides a direct electromagnetic drive of driven components, such as the inner tilt frame 12, with no backlash, lost motion and/or hysteresis.

In particular, as shown in FIG. 3, the first motor 22 has a stationary stator 23 opposing the inner wall of an inner bore 15 of the motor housing 18 and a rotatable rotor 24, which is attached to a frame motor shaft 28 keyed to the inner tilt frame 12 for synchronous displacement therewith. Note that because an angular distance, at which the inner tilt frame displaces, does not exceed 5–10°, it is possible to utilize the brushless first motor 22 so that the rotatable rotor 24 rotates relative to the stationary stator 23, and not otherwise as is typically the case with the brushless motors. The motor shaft 28 is fixed to the rotatable rotor 24 and is journaled at its opposite ends in the motor housing 18 and the outer frame 16 by means of two spaced radial ball bearings 26, which are preferably high precision ball bearings. Retainers 29 and 30, such as rings and springs, positioned at opposite axial ends of the rotatable rotor 24 prevent axial displacement of the first motor 22 relative to frame motor shaft 28. Accordingly, the first motor 22 is biased inwards from the ball bearings 26 to minimize their damage due to accidental contact with first motor.

The inner tilt frame 12 may have a one-piece peripheral wall or a plurality of adjoining walls defining an inner space, which receives the platform 14. Accordingly, the frame motor shaft 28 terminates within the periphery of the inner tilt frame 12 without extending into the inner space and, thus, does not prevent angular displacement of the platform 14 about the platform axis 13 within the inner space. To stabilize a position of the inner tilt frame 12 relative to the outer frame 16, a positioning flange 32 coaxial with the frame motor shaft 28 is fixed to the inner tilt frame 12. The ball bearing 26 mounted on the outer frame 16 rotationally supports the positioning flange 32 and allows this flange to move synchronously with the inner tilt frame 12 relative to the outer stationary frame 16. Accordingly, the inner tilt frame 12 and the positioning flange 32 rotate synchronously in response to actuation of the first motor 22.

A positioning control of the inner tilt frame 12 is provided by a combination of a scale holder 34 with a grating scale 35, which is made from a material having a reflective surface provided, in turn, with a plurality of grits, and a frame read head 36. The scale holder 34 is rigidly mounted to the outer end of the positioning flange 32 and thus rotates synchronously with the inner tilt frame 12. The position feedback required for the first motor 22 is accomplished by securing the frame read head 36 mounted stationary on a hub 38, which is attached to the outer frame 16, and opposing the grating scale 35. The frame read head 36 is provided with a solid state sensor having a light source transmitter, which generates a beam of light directed at the displaceable grating scale, a receiver or decoder receiving a reflective beam and capable of decoding a number of counts corresponding to a desired angular path of the inner tilt frame 12 and electronics capable of determining a direction of rotation of the frame. Such solid-state sensors are known in the art.

Alternatively, the grating scale 35 can be mounted directly on an outer side of the inner tilt frame 12, as shown in dash lines in FIG. 3, whereas the frame read head 36 can be attached to the inner surface of the side 17 of the outer frame in a juxtaposed relationship with the grating scale 35.

Figure 4:
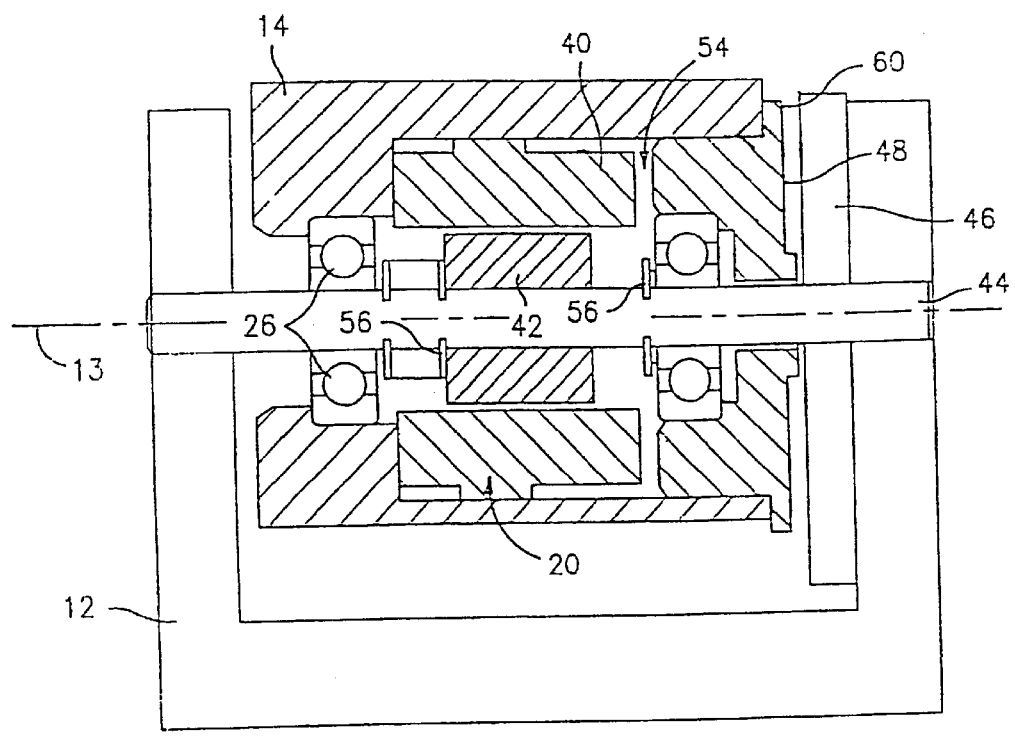
FIG. 4 is axial view of the precision positioning tilt device of FIG. 1 taken along a platform axis extending perpendicular to the frame axis.

Referring to FIG. 4, to provide synchronous displacement of the platform 14 with the inner tilt frame 12 about the frame axis 11 in response to actuation of the first motor 22, a central stationary platform shaft 44 extending along the platform axis 13 is fixed to the inner tilt frame 12 and to a stationary rotor 42 of a second motor 20. Accordingly, as the inner tilt frame 12 rotates about the frame axis 11, the platform shaft 44, coupling the inner frame 12 and the platform 14 in the direction B (FIG. 1), translates this motion into tilting motion of the platform 14 about the axis 11.

The platform shaft 44 supports a platform actuating system including the second motor 20, which is also an electric DC brushless servo torque motor operative to swing the platform 14 about the platform axis 13. The second motor 20 is mounted within a cavity 54 defined by an inner surface of the platform 14, which thus serves as a motor housing, and includes the stationary rotor 42 surrounding and attached to the stationary platform motor shaft 44 by a pair of spaced retainer rings 56. In addition to the stationary rotor 42, the second motor 20 further includes a rotatable stator 40 fixed to the platform 14 to enable the angular displacement of the platform in response to actuation of the second motor 20. Displacement of the stator 40 and, thus, the platform 14 relative to the rotor 42 is accomplished by mounting spaced ball precision bearings 26 between the platform 14 and the stationary shaft 44. Accordingly, once the second motor 20 is energized independently from the first motor 22, the stator 40 of the second motor 20 and the platform 14 are enabled to pivot relative to the inner tilt frame 12 about the platform axis 13.

Figure 5:
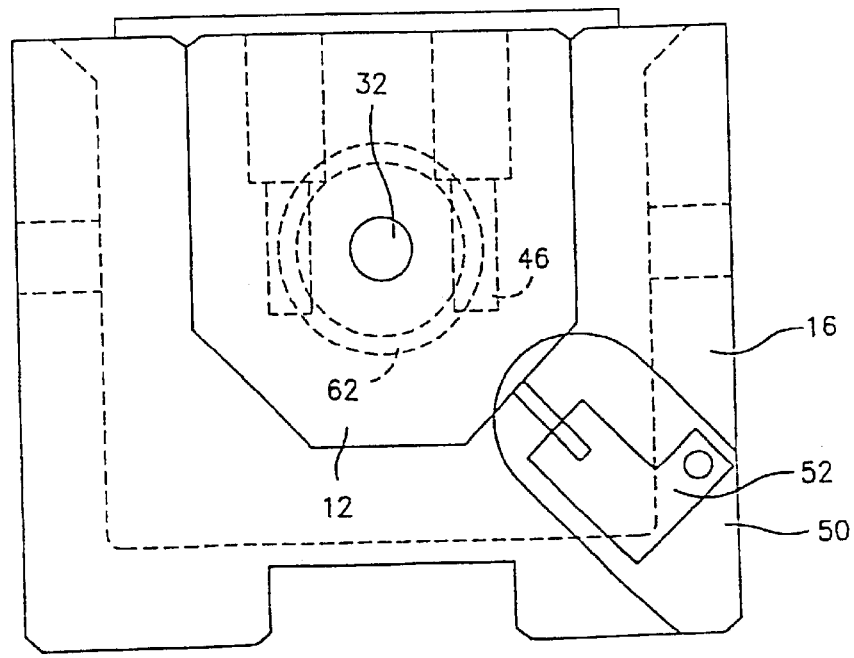
FIG. 5 is a side elevation view of the precision positioning tilt device illustrating a scale holder along with an end switch designed to limit angular displacement of a respective tiltable part of the tilt device.

Similarly to the first motor 22, the second motor 20 is provided with the position feedback required for a servomotor. As shown in FIG. 5, the position feedback system includes a stationary non-contacting electronic position sensor 46 mounted to the stationary platform shaft 44 and a platform scale holder 48 mounted on a side 60 of the platform which faces the inner tilt frame 12. The platform scale holder 48 has a circular grating scale 62 opposing the position sensor 46, which, like the frame read head 36, includes a light beam transmitter and a decoder, as well known in the art.

Both the platform 20 and frame 22 motors can be provided with end switches 52 arresting angular displacement of the inner tilt frame 12 and platform 14. The end switch 50 can be mounted stationary on the inner tilt frame 12 for controlling displacement of the platform 14 and on the outer frame 16 for controlling displacement of the inner tilt frame 12. The end switch 50 is provided with a source 52 generating a light beam that, when intercepted by the displaceable scale holder moving through a beam path, prevents further displacement of either the inner tilt frame 12 or the platform 14. Alternatively, a central processing unit (CPU) 63 (FIG. 3) is provided with software operative to automatically stop angular displacement of the pivotal components of the positioning tilt device 10.

The precision positioning device 10 can operate as a single tilt stage including either the platform 14 or the inner frame 12 or, as is disclosed above, as a dual tilt stage. Furthermore, the positioning device 10 can be a module electronically and mechanically connectable with a variety of different modules to form a larger unit capable of performing different tasks besides tilting the element 15 in two planes.

In operation, the element 15, which can be an optical fiber to be connected to or aligned with a coupler or a surgical instrument or any other element in a predetermined manner, is placed on the platform 14 for further spatial adjustment in accordance with data inputted in the CPU 63. A shape and size of the platform 14 is selected in response to a given application. The CPU 63 generates a signal corresponding to a desired angular displacement of the elements to be connected or aligned. The generated signal sequentially or selectively actuates the second 20 and first 22 motors, the angular displacement of which are monitored by the platform 46 and frame 36 read heads capable of determining a direction of rotation and calculating counts representing the desired angular displacement of the platform 14 and the inner tilt frame 12, respectively. Once the count is completed, further displacement of the monitored components is prevented. Positioning the frame 34 and platform 48 scale holders coaxially with the frame 12 and platform 14, respectively, substantially facilitates monitoring of their angular displacement.

Various changes and modifications may be effected in the invention by one skilled in the art without departing from the scope of the invention as recited in the appended claims.

What is claimed is:

1. A precision positioning tilt device comprising:
   an outer frame;
   a tilt frame mounted pivotally on the outer frame to pivot about a frame axis; and
   a platform mounted on the tilt frame and selectively pivotable about the frame axis and about a platform axis extending coplanar with and transversely to the frame axis, whereas the frame and platform axes intersect one another within the platform.

2. The device according to claim 1, further comprising a first motor mounted to the outer frame and actuating the tilt frame and the platform to synchronously tilt about the frame axis.

3. The device according to claim 2, wherein the first motor is a servo motor received in a motor housing, which is attached to the outer frame and extends outwardly therefrom along the frame axis.

4. The device according to claim 3, wherein the first motor has a frame motor shaft rotatable about the frame axis and having opposite ends journaled in the motor housing in a first ball bearing and in the outer frame in a second ball bearing, respectively, the first motor shaft being fixed to the tilt frame so that when the first motor is actuated, the frame motor shaft and the tilt frame rotate synchronously about the frame axis.

5. The device according to claim 4, wherein a respective precision ball bearing is mounted on each of the opposite ends of the frame motor shaft to provide the rotation of the frame motor shaft relative to the motor housing and to the outer frame.

6. The device according to claim 3, wherein the motor housing has an inner bore receiving the first motor, the device further comprising two retaining elements spaced axially apart in the inner bore and mounted to position the first motor in the motor housing.

7. The device according to claim 6, wherein the retaining elements include a pair of springs mounted on the opposite ends of the frame motor shaft and extending between the first and second balls bearings and a first motor stator of the first motor, the retaining elements further include spaced retainer rings coupling the frame motor shaft and a first motor rotor of the first motor.

8. The device according to claim 4, wherein the tilt frame has a positioning flange fixed to the tilt frame coaxially with and spaced from the frame motor shaft, the positioning flange extending axially outwards from the tilt frame and through the outer frame and is journaled on a respective precision ball bearing mounted on the outer frame to rotate relative to the outer frame as the tilt frame tilts about the frame axis.

9. The device according to claim 8, further comprising a position feedback control system coupled to the first motor and including a scale holder, which is fixed to an outer end of the positioning flange to rotate synchronously therewith, and a positioning sensor secured to the outer frame and operative to generate an output signal disabling the angular displacement of the first motor upon reaching a desired angular position of the tilt frame.

10. The device according to claim 9, wherein the outer frame has a hub extending parallel to the positioning flange and beyond the scale holder so that the positioning sensor, which is mounted stationary to an outer end of the hub, opposes the displaceable scale holder having a surface made of refectory material and provided with a plurality of grids.

11. The device according to claim 1, wherein the platform has a cavity receiving a second motor providing angular displacement of the platform about the platform axis independently from angular displacement of the tilt frame.

12. The device according to claim 11, wherein the second motor is an electric DC brushless servo torque motor positioned centrally within the platform and having a stationary inner rotor and a rotatable outer stator, which is coupled to the platform for synchronous angular displacement therewith.

13. The device according to claim 12, wherein the second motor further has a platform motor shaft coupled to the stationary inner rotor of the second motor and having opposite ends fixed to the tilt frame.

14. The device according to claim 13, further comprising two spaced precision ball bearings mounted between an inner surface of the platform and the platform motor shaft to enable angular displacement of the platform relative to the platform motor shaft.

15. The device according to claim 12, further comprising a closed loop servo control system including a non-contacting electronic position sensor fixed to one of the opposite ends of a shaft of the second motor.

16. The device according to claim 15, wherein the platform has a side opposing the non-contacting electronic position sensor and provided with a circular grating scale which is fixed to the side to tilt about the platform axis relative to the non-contacting electronic sensor.

17. The device according to claim 1, wherein the outer frame and the tilt frame each has a respective end switch arresting angular displacement of the tilt frame relative to the outer frame and relative angular displacement of the platform relative to the tilt frame.

18. The device according to claim 1, wherein the platform has an axis of symmetry, the point of intersection of the frame and platform axes being located on the axis of symmetry.

* * * * *